(12) United States Patent
Huber et al.

(10) Patent No.: US 8,798,703 B2
(45) Date of Patent: Aug. 5, 2014

(54) DISPOSABLE AND DETACHABLE SENSOR FOR CONTINUOUS NON-INVASIVE ARTERIAL BLOOD PRESSURE MONITORING

(75) Inventors: Christian Huber, Graz (AT); Rupert Grüllenberger, Graz (AT); Jürgen Fortin, Graz (AT)

(73) Assignee: CNSystems Medizintechnik AG, Graz (AT)

( * ) Notice: Subject to any disclaimer, the term of this patent is extended or adjusted under 35 U.S.C. 154(b) by 279 days.

(21) Appl. No.: 13/226,596

(22) Filed: Sep. 7, 2011

(65) Prior Publication Data

US 2012/0059233 A1 Mar. 8, 2012

Related U.S. Application Data

(60) Provisional application No. 61/380,511, filed on Sep. 7, 2010.

(51) Int. Cl.
*A61B 5/00* (2006.01)
*A61B 5/02* (2006.01)
*A61B 5/022* (2006.01)
*A61B 5/0225* (2006.01)

(52) U.S. Cl.
CPC ....... *A61B 5/02241* (2013.01); *A61B 2562/164* (2013.01); *A61B 5/6826* (2013.01); *A61B 2560/0443* (2013.01); *A61B 2560/0406* (2013.01); *A61B 5/02255* (2013.01); *A61B 5/6831* (2013.01)
USPC .......................... 600/323; 600/490; 600/492

(58) Field of Classification Search
None
See application file for complete search history.

(56) References Cited

U.S. PATENT DOCUMENTS

| | | | | |
|---|---|---|---|---|
| 5,048,533 A | * | 9/1991 | Muz | 600/492 |
| 5,218,966 A | | 6/1993 | Yamasawa | |
| 5,437,275 A | * | 8/1995 | Amundsen et al. | 600/323 |
| 5,991,648 A | * | 11/1999 | Levin | 600/344 |
| 6,095,974 A | | 8/2000 | Shemwell et al. | |
| 6,253,097 B1 | * | 6/2001 | Aronow et al. | 600/310 |
| 6,285,894 B1 | * | 9/2001 | Oppelt et al. | 600/322 |
| 6,321,100 B1 | * | 11/2001 | Parker | 600/344 |
| 6,322,515 B1 | * | 11/2001 | Goor et al. | 600/485 |
| 6,343,224 B1 | * | 1/2002 | Parker | 600/344 |
| 6,377,829 B1 | * | 4/2002 | Al-Ali | 600/323 |

(Continued)

FOREIGN PATENT DOCUMENTS

JP 9 289977 A 11/1997
WO 03/001180 A2 1/2003

OTHER PUBLICATIONS

The International Preliminary Report on Patentability for PCT/IB2011/002720 dated Mar. 21, 2013.

*Primary Examiner* — Jacqueline Cheng
*Assistant Examiner* — Corey B Hipps
(74) *Attorney, Agent, or Firm* — McDonnell Boehnen Hulbert & Berghoff LLP

(57) ABSTRACT

A sensor system for continuous non-invasive arterial blood pressure (CNAP) is provided. The CNAP-sensor comprises of a base portion and a detachable and disposable portion. The base portion is connected to a control system. The disposable portion is for attachment to a human body part. The CNAP-sensor system includes a photo-plethysmographic (PPG) system having at least one light source, at least one light detector, electrical supplies, light coupling systems, one or more connectors, and a cuff including air supplies.

10 Claims, 9 Drawing Sheets

(56) References Cited

U.S. PATENT DOCUMENTS

| | | | |
|---|---|---|---|
| 6,526,309 B1 * | 2/2003 | Chance | 600/473 |
| 6,669,648 B1 * | 12/2003 | Fortin et al. | 600/490 |
| 6,931,268 B1 * | 8/2005 | Kiani-Azarbayjany et al. | 600/316 |
| 6,939,304 B2 * | 9/2005 | Schnall et al. | 600/481 |
| 7,164,938 B2 * | 1/2007 | Geddes et al. | 600/324 |
| 7,351,206 B2 * | 4/2008 | Suzuki et al. | 600/500 |
| 7,390,301 B2 * | 6/2008 | Skrabal et al. | 600/490 |
| 8,185,182 B1 * | 5/2012 | Shankar | 600/347 |
| 8,277,388 B2 * | 10/2012 | Muramatsu et al. | 600/504 |
| 8,414,499 B2 * | 4/2013 | Al-Ali et al. | 600/504 |
| 2004/0267105 A1 * | 12/2004 | Monfre et al. | 600/344 |
| 2006/0079794 A1 * | 4/2006 | Liu et al. | 600/502 |
| 2006/0129039 A1 * | 6/2006 | Lindner et al. | 600/323 |
| 2006/0195034 A1 * | 8/2006 | Skrabal et al. | 600/485 |
| 2007/0123756 A1 * | 5/2007 | Kitajima et al. | 600/300 |
| 2007/0191720 A1 * | 8/2007 | Muramatsu et al. | 600/504 |
| 2008/0076981 A1 * | 3/2008 | Hoarau | 600/310 |
| 2008/0076988 A1 * | 3/2008 | Sarussi et al. | 600/323 |
| 2008/0188760 A1 * | 8/2008 | Al-Ali et al. | 600/507 |
| 2009/0018421 A1 * | 1/2009 | Sarussi et al. | 600/324 |
| 2009/0118603 A1 * | 5/2009 | Matlock | 600/323 |

* cited by examiner

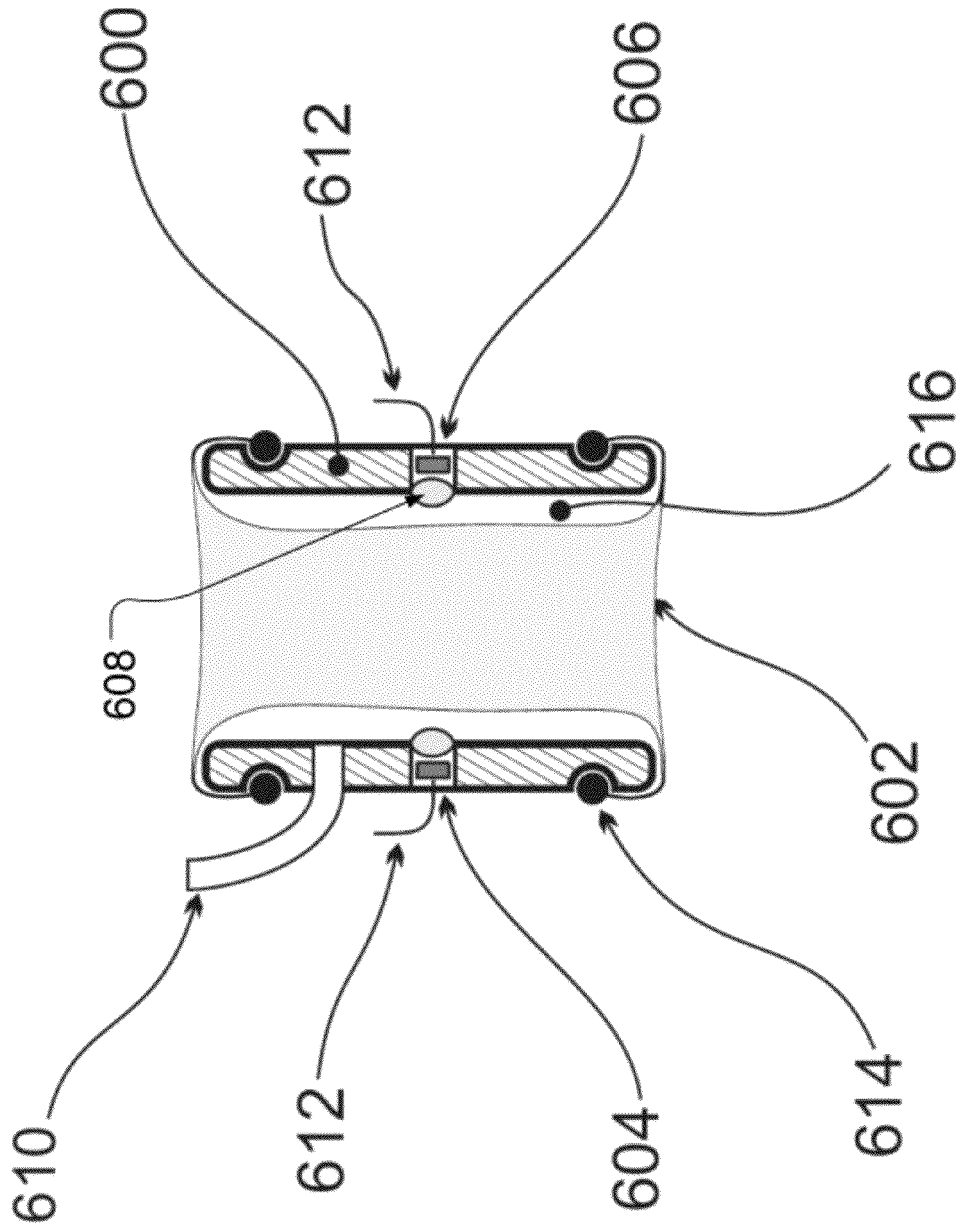

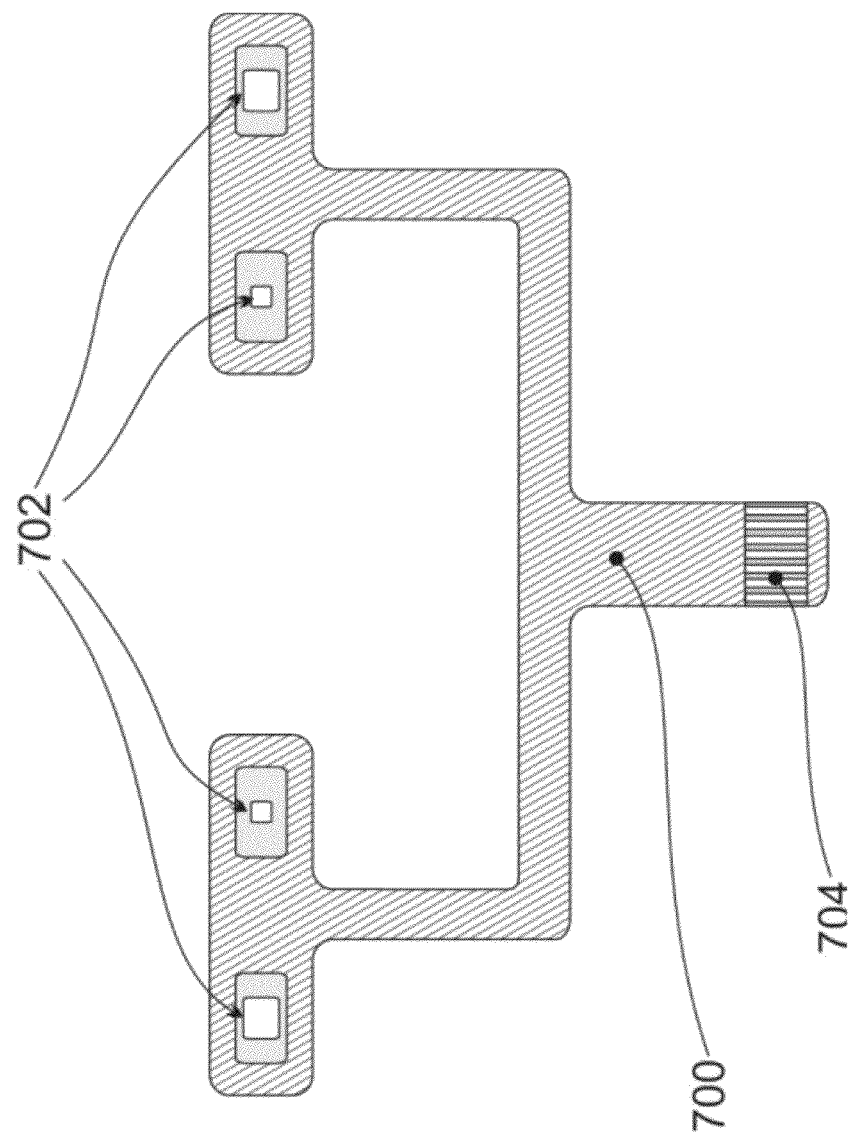

DISPOSABLE AND DETACHABLE SENSOR FOR CONTINUOUS NON-INVASIVE ARTERIAL BLOOD PRESSURE MONITORING

CROSS REFERENCE TO RELATED APPLICATIONS

The present application is a non-provisional of U.S. provisional patent application Ser. No. 61/380,511 filed Sep. 7, 2010, the entire contents of which are incorporated herein by reference.

BACKGROUND

1. Field

The invention relates generally to a sensor for measuring blood pressure and derived hemodynamic parameters, and more particularly to a continuous non-invasive arterial pressure (CNAP) measurement, where the sensor is disposable.

2. Description of Related Art

Blood pressure (BP) may be measured in a number of ways. As one example, a standard non-invasive sphygmomanometer (NBP) may be placed on the upper arm or wrist. The NBP applies pressure to the arteries, causing them to constrict and limit blood flow. As the pressure is released, blood flow is restored in the artery, and the systolic and diastolic blood pressures may be measured. NBP measures BP intermittently and not continuously.

Invasive devices may also be used to measure blood pressure, such as an intra-arterial catheter, for example. Invasive Blood Pressure (IBP) devices can be painful to the patient.

Another device for measuring blood pressure is a sensor having a cuff, an infrared light source, and a light detector for measuring a photo-plethysmographic (PPG) signal. This type of signal is known from pulse oximetry (PO). The PPG-signal is fed into a control system, which produces a counter-pressure in the finger cuff. It is well known that the counter pressure equals intra-arterial pressure when the PPG-signal is kept constant. Thus, the counter pressure, which is indirect equivalent to intra-arterial BP, is measured. This method is known as "Vascular Unloading Technique" or "Continuous Non-Invasive Arterial Pressure" (CNAP). This method combines the advantages of both previous methods NBP and IBP; it delivers continuous BP-information and it is painless due to its non-invasive nature.

A CNAP-sensor system is typically placed over an artery of the human body (e.g. at the finger). The sensor system includes a cuff having air supplies and a PPG system. The PPG system may include at least one light source, at least one light detector, electrical components, and one or more connectors. The sensor system is further connected to a control system, which provides an electrical interface and air supply. For a better light transmission, light coupling systems can be used. When the sensor has to be replaced (e.g. for hygienic reasons) all components have to be replaced. Thus, it would be desirable to create a disposable and detachable sensor system.

SUMMARY

A CNAP-sensor system is disclosed including a base portion and a disposable and detachable portion. The base portion is reusable and is connected to a control system. The disposable portion is attached to the human body and designed for low price production. The CNAP-sensor system includes a cuff including air supplies, a PPG system having at least one light source and at least one light detector including electrical supplies, light coupling systems, and one or more connectors.

In one embodiment, the sensor includes a reusable base portion connected to a measurement unit and a detachable portion secured to the base portion. The detachable portion is adapted to receive a human body part and is also disposable. The sensor system includes a plethysmographic (PPG) system. The PPG system includes at least one light source, at least one light detector, an electrical connector to connect the at least one light source to an electrical supply, and an air system. At least a part of the PPG system is located on the base potion and at least a part of the PPG system is located on the detachable portion.

In a further embodiment, the reusable base portion includes both the light detector and light source, an air-supply, electrical cables or carriers, and connectors to the control system. A detachable and disposable cuff that contains a fiber optic system for transmitting light to and from the finger is mounted on the base portion.

In another embodiment, the base portion is in the form of a semi-rigid tube, which contains a light source and detector, an air supply, and light coupling systems. The disposable part is a material having thick ends with flexible torus-shaped rings.

In yet another embodiment, the base portion includes a cuff having an air-supply and an air-connector. The disposable part is made of plaster and contains one or more light sources and detectors.

BRIEF DESCRIPTION OF THE FIGURES

An exemplary embodiment of the present invention is described herein with reference to the drawings, in which:

FIG. 6 shows a sensor system with a disposable material;

FIG. 7 illustrates a disposable double finger plaster in accordance with another embodiment of the present application.

DETAILED DESCRIPTION

A sensor system for measuring continuous non-invasive arterial blood pressure (CNAP) is described. The CNAP-sensor system comprises a fixed part or reusable base portion and a detachable and disposable portion. The reusable base portion is connected to a control system and contains costly components. The detachable and disposable portion is for attachment to a human body part, such as a finger, and designed to be low in cost.

In general, the CNAP-sensor system transmits light from a light source (preferably infrared) through a finger and receives the transmitted light with a light detector. At the same time, a variable counter pressure is applied to the finger over an air-cuff that encloses the finger. Thus, a CNAP-sensor system may include a photo-plethysmographic (PPG) system having at least one light source, at least one light detector, electrical supplies, light coupling systems, one or more connectors, and a cuff having air supplies. The electrical supplies may include cables or flexible print circuits, for example.

Figure 1:
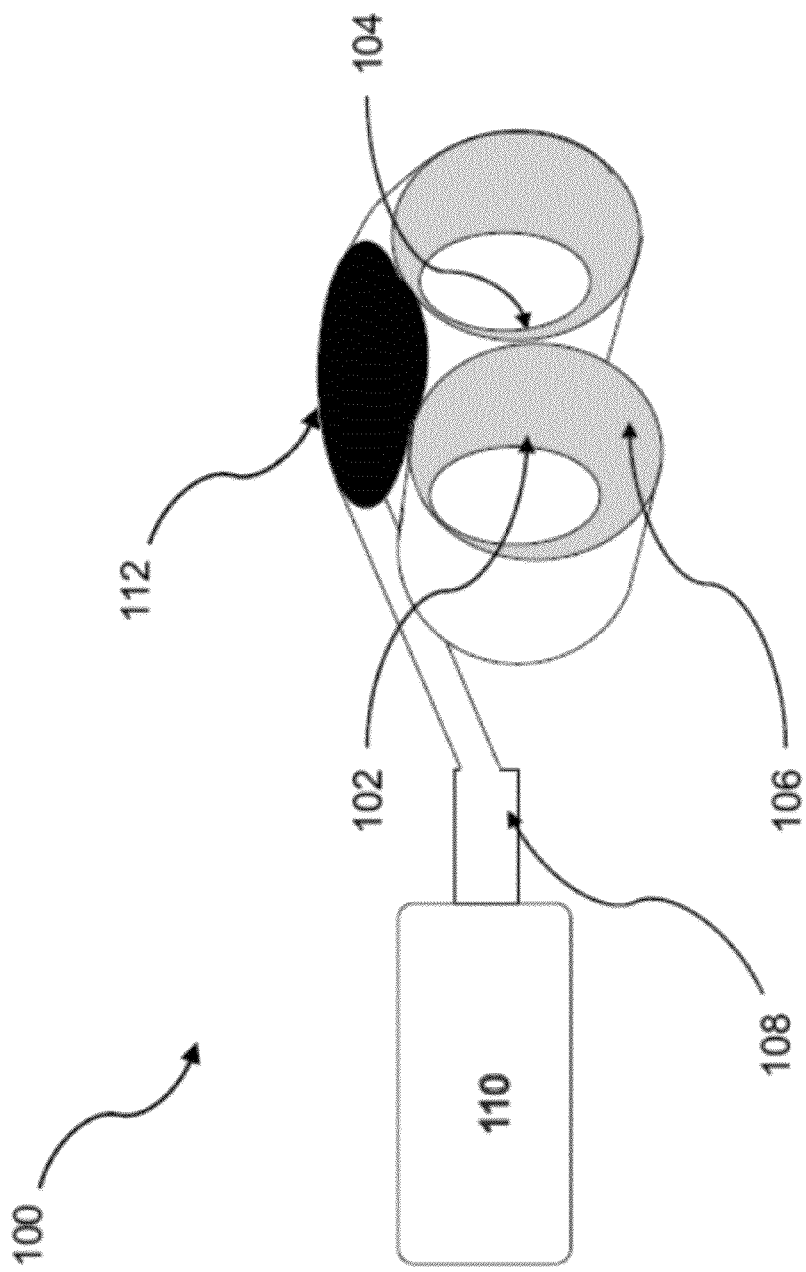
FIG. 1 illustrates an example of a prior art sensor for measuring blood pressure using a double cuff for measuring blood pressure in a finger.

FIG. 1 shows a prior art CNAP sensor 100 configured as a double finger sensor. The sensor 100 includes a PPG system having at least one light source 102, at least one light detector 104, electrical supplies, light coupling systems, a cuff 106 having air supplies, a cap 112, and a connector 108 to the control system 110. Light is shone through the finger in order to measure arterial blood volume. The light source 102 is preferably an LED having a wave length between 650-1000 nm. Typically the wavelength is around 840 nm, where hemoglobin and oxyhemoglobin have their isobestic point. Red blood cells absorb light from that wavelength regardless of whether the cells carry oxygen (oxyhemoglobin) or not (hemoglobin). When the sensor is used for a pulse oximetry function, different multiple wavelengths like 650 nm and 960 nm are preferred. A different control system may be used for that purpose, such as the system disclosed in U.S. Pat. Pub. No. 2008/0200785.

The light detector 104 measures the amount of light from the light source 102 that is not absorbed by arterial blood (red blood cells), and produces an inverse function of arterial blood flow in the finger. This signal is also a measure of the diameter of the artery. The light detector 104 can be, for example, a photodiode that converts the receiving light to a small electrical current (photocurrent). The photocurrent is transported to the control system 110 and amplified. The signal-to-noise ratio is low and a shield for preventing distortion may be used. Instead of a photodetector, a Light-to-Frequency Converter (LFC) can be used as the light detector 104. An LFC is an integrated circuit that modulates the digital output signal by the received light. As the digital signal is not that influenced by surrounding noise, electrical shields can become obsolete.

The sensor 100 directs light into the finger tissue and receives the transmitted light and transmits it to a receiver. If the transmitting or receiving component has no direct contact to the finger, a light coupling system may be used. A light coupling system can be any sort of optical arrangement or combination that helps guide the light between the sensor and the tissue, such as fiber optics or lenses, for example. In another example, a transparent fluid can be used to fill the gap between the finger tissue and optical components.

A gas-filled air-cuff 106 applies variable pressure to the finger. The pressure is adjusted by the control system 110 and is equal to the blood pressure inside the finger during measurement mode. For optimal pressure transmission, the air-cuff 106 encloses the finger as a ring. The ring-shaped outer layer may be more rigid than the inner layer of the air cuff 106, which has direct contact to the skin. Air pressure is transmitted to the air cuff 106 by an air supply, such as a pump connected to a valve system, for example. The air pressure is preferably transmitted through an air tube. The tube may be flexible, such as a silicone hose, to prevent movement of artifacts.

The connector 108 connects the sensor 100 and the control system 110. As shown here, the connector 108 can carry both electrical and air signals. In other configurations, separate connectors for electric and air signals can be used.

The control system 110 is not part of the CNAP sensor. The control system 110 receives the inverse arterial flow (volume) signal and reacts with a pressure in the air-cuff 106. It is known from the art that the cuff pressure is equal to the arterial pressure, when the arterial volume signal is kept (clamped) constant. Therefore, this method is sometimes called the "volume clamp method".

Figure 2:
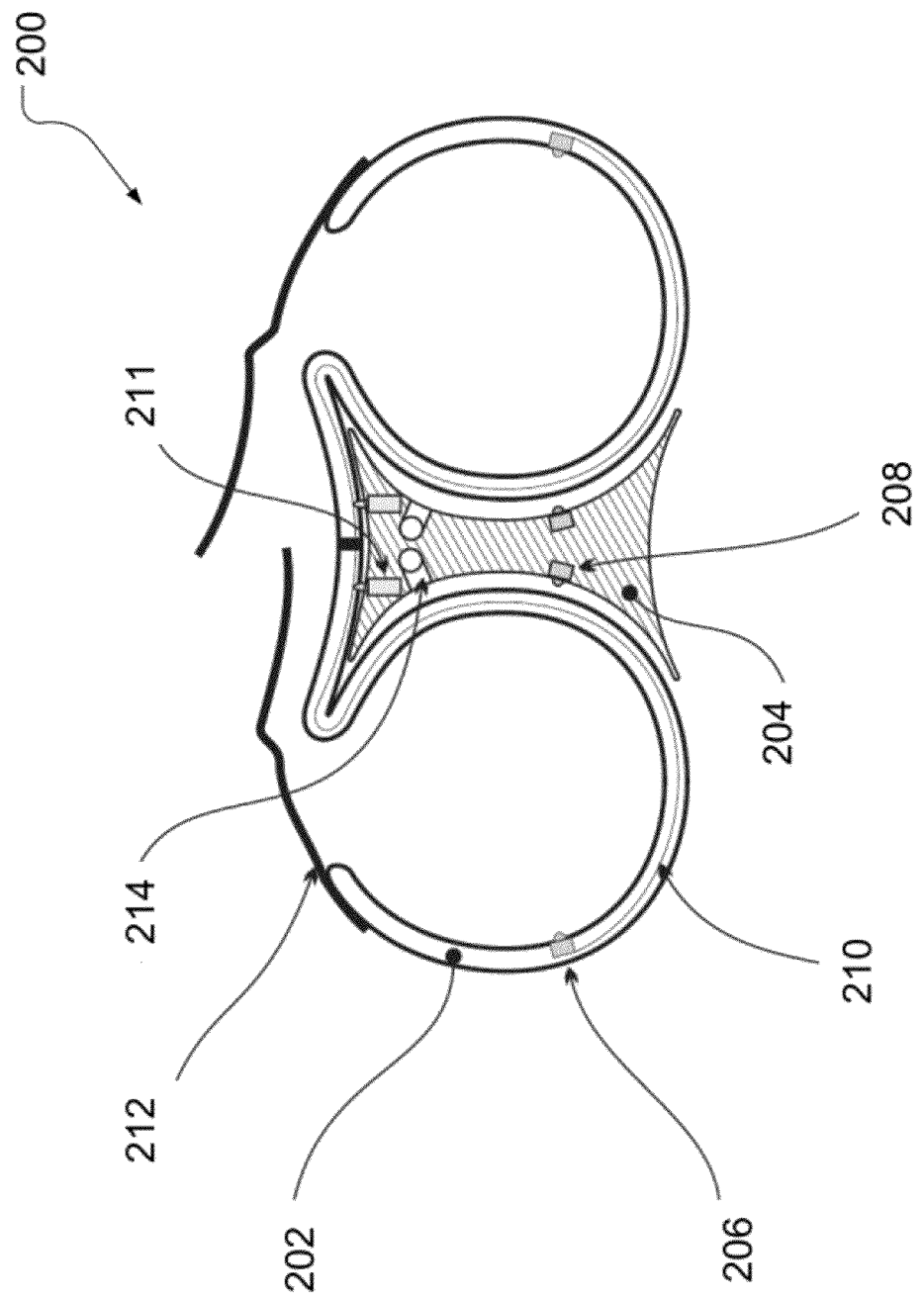
FIG. 2 shows a sensor of the present application, where the sensor is a double finger cuff.

FIG. 2 shows the front view of one embodiment of an example sensor system 200 of the present application configured as double finger cuff. Although the sensor system is shown as finger sensors and a double finger cuff, it should be understood that a single cuff may alternatively be used, as well as sensors measuring elsewhere on the body of a human or animal. A detachable and disposable cuff, or w-shaped part, 202 encloses two neighbored fingers. The cuff 202 is preferably made of plastic or other formable material with consideration to bio-compatibility due to the contact with the human body. The cuff 202 is mounted on a base portion 204, which in this embodiment in x-shaped. The cuff 202 may be mounted to the base portion 204 by snap fasteners or other types of connectors.

One or more light sources 206 are mounted to the cuff 202. The light sources 206 may be light emitting diodes (LEDs) or laser diodes, for example. The base portion 204 may include one or more light detectors 208, which are located opposite to the light sources 206. The light sources 206 may be connected to an electrical supply 211 by electrical connectors 210, such as wires, for example. The electrical connectors 210 may be formed as part of the cuff 202. The cuff 202 may be secured to fingers with a fastener 212, such as an adhesive tape, VELCRO®, hook and loop fastening device, or a fastening clip over the fingers. Alternatively, any known fastener may secure the cuff 202 to the fingers. The base portion 204 may also include an air tube 214 for supplying air to the cuff 202 from an air supply (not shown) in order to produce pressure to the finger.

Figure 3:
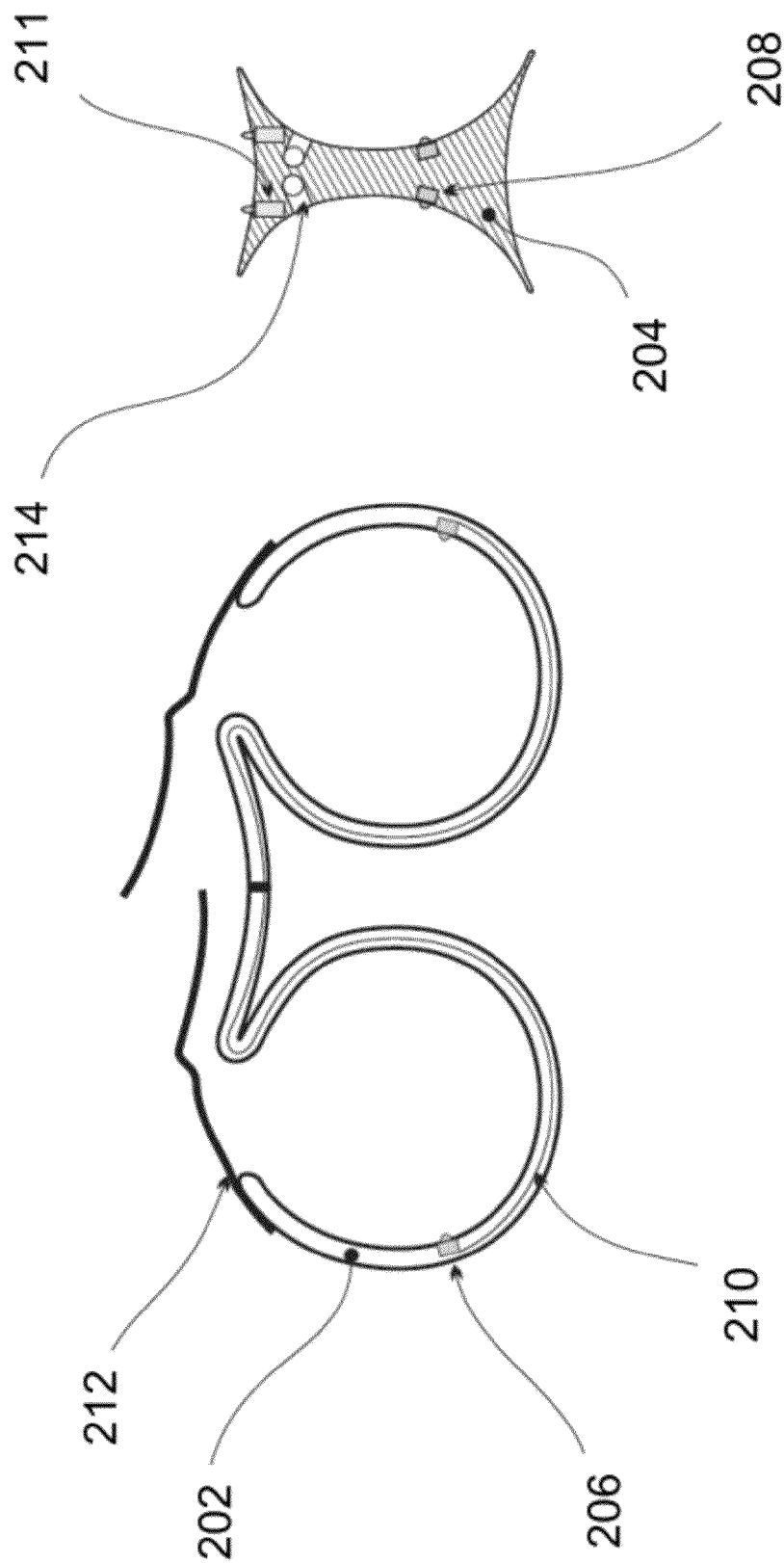
FIG. 3 illustrates the cuff of FIG. 2 removed from the base portion.

FIG. 3 shows the cuff 202 detached from the base portion 204. The cuff 202 includes only the light sources 206, which may be LEDs, and the electrical connectors 210. In one embodiment, the cuff 202 does not include any electrical components. In another embodiment, the cuff 202 can include the light detectors 208 instead of or in addition to the light source 206.

Figure 4:
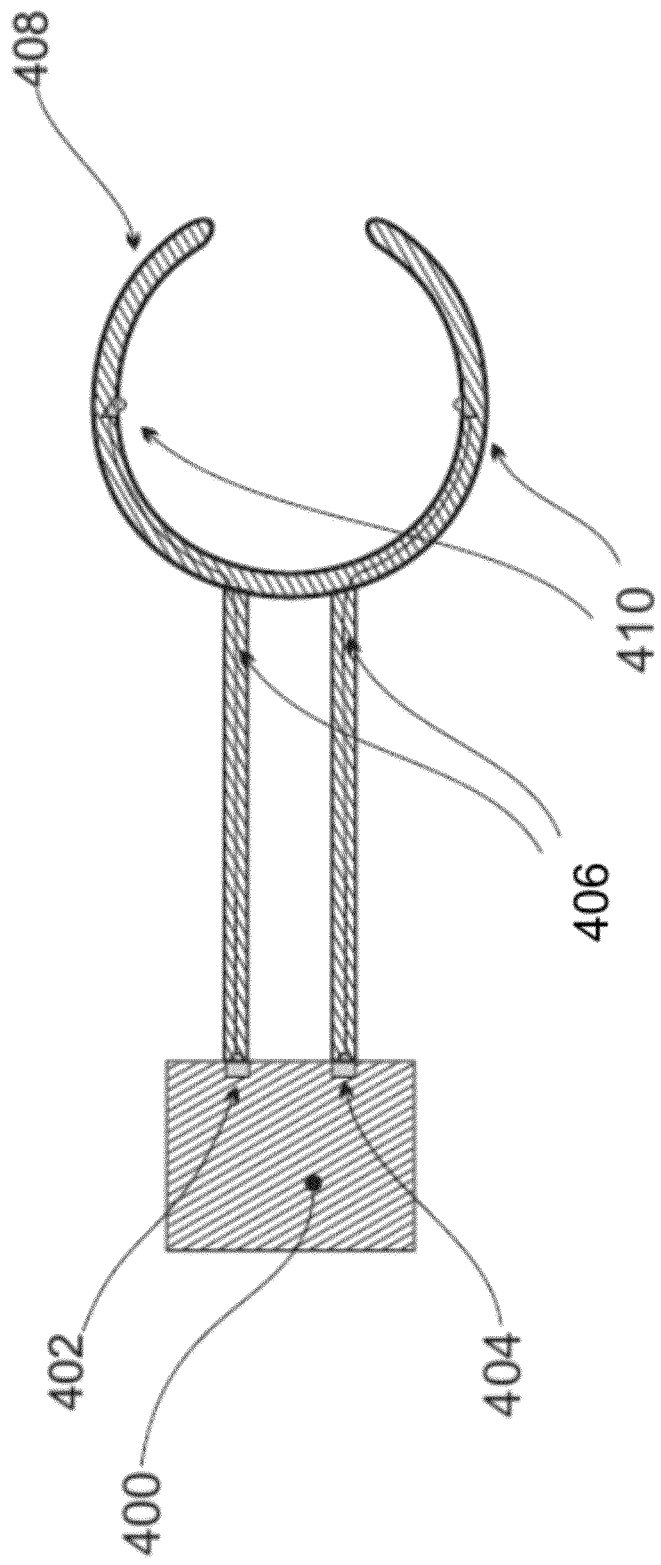
FIG. 4 shows a schematic of a fiber optic system.

FIG. 4 shows an example of a fiber optic system that can be used for plethysmography. The base portion 400 includes both a light source 402 and a light detector 404. Optical fibers 406 carry light to and from a portion 408 that could be detachable and disposable. The fiber optics may require additional light guides 410 at the fiber end for light propagation from and to the finger tissue. The finger is placed between both ends for light propagation.

Figure 5:
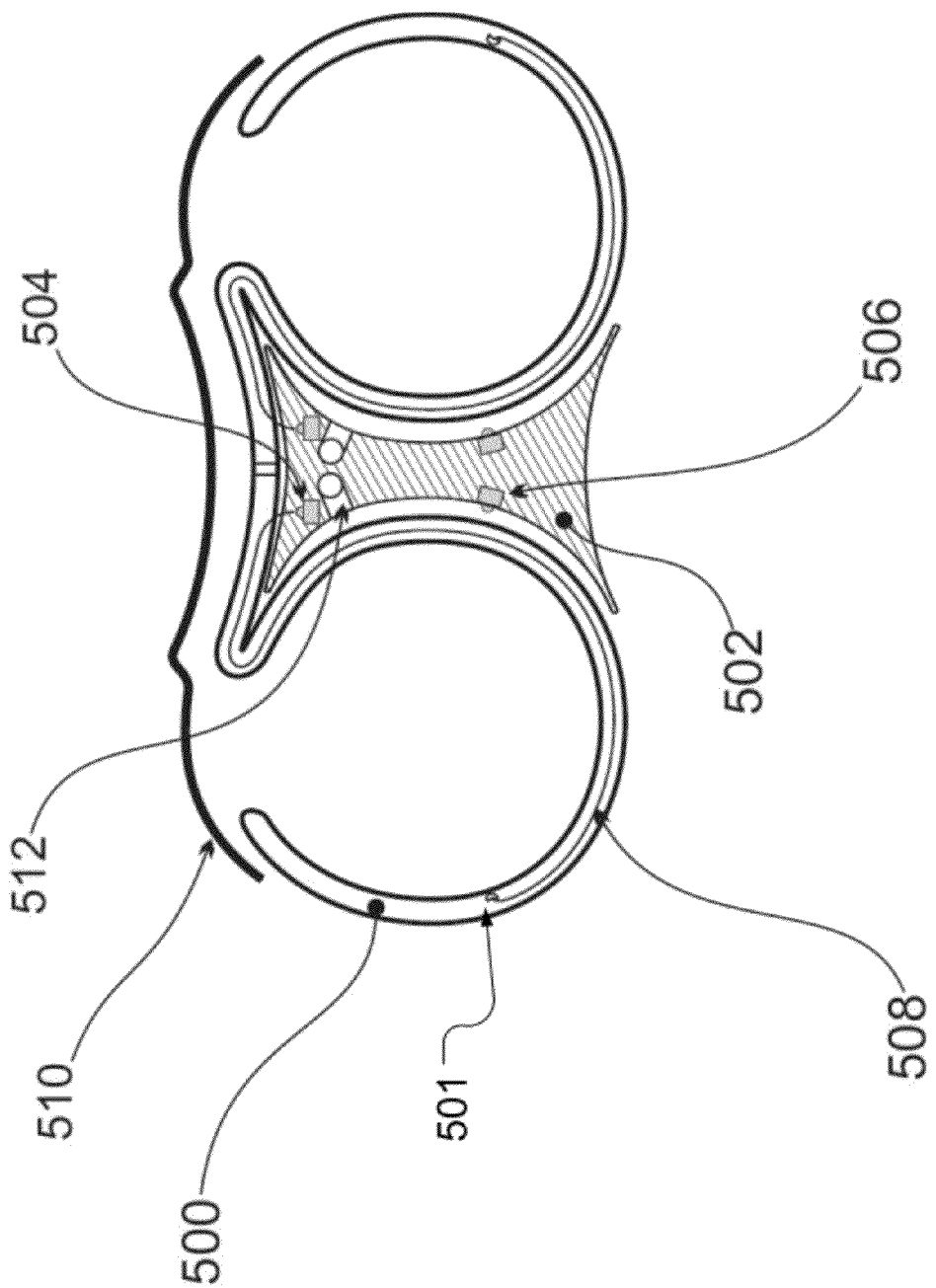
FIG. 5 illustrates a detachable air-chamber having a fiber optic system.

FIG. 5 shows the front view of another embodiment using the fiber optic concept. A detachable and disposable portion 500, which may be an air-cuff, is mounted on a base portion 502. In contrast to the embodiment shown in FIGS. 2 and 3, light sources 504 and light detectors 506 are included in the base portion 502. The cuff 500 includes optical fibers that transport light to outer edges of the cuff, opposite from the light detectors 506. Thus, light can be transmitted through the finger from the end 501 of the optical fiber in the outer edge of the cuff 500 to the light detector 506. Again, the cuff 500 may be secured to fingers with a fastener 510, such as an adhesive tape, VELCRO®, hook and loop fastening device, or a fastening clip over the fingers, for example. The base portion 502 also includes an air tube 512 for supplying air to the cuff 500. In another example, the optical fibers themselves may receive light from the finger and transport it to the light detectors 506.

Yet another embodiment of the system is shown in FIG. 6. This embodiment includes a semi-rigid tube 600 as the base portion and a detachable and disposable material 602 placed around the base portion. The semi-rigid tube 600 contains the light source 604 and light detector 606. For an optimal light transmission to and from the finger, light coupling systems 608 may be located adjacent the light source 604 and the light detector 606. In one embodiment, the light coupling systems 608 may be lenses. An air supply system or air tube 610 and electrical supplies 612 may also be located inside the semi-rigid tube 600.

In one example, the material 602 may be a hose having thick ends, with flexible torus-shaped rings 614, which may be comparable to the end of a balloon. For the application, the material 602 is placed over the finger and the semi-rigid tube 600 is slipped over the material 602. The torus-shaped rings 614 of the material are put over the end of the tube 600 and held in place by notches (not shown) outside of the tube 600. This procedure, which can be performed by the user, forms the air-chamber 616.

Another embodiment is shown in FIG. 7. In this embodiment, a detachable and disposable portion 700 includes electrical components 702, e.g., light sources and light detectors, as well as simple connectors 704. An air system (cuff, supply and connector) is located in the base portion (not shown). This concept is known from SpO2-probes, where all components are placed on an adhesive tape or plaster. The disposable portion 700 is formed as a double finger plaster. The plaster may be made of a flexible print circuit that carries the electrical connection and wires. The plaster is positioned on the finger, with the light detectors positioned opposite to the light sources. The air system is then placed over the plaster.

The plaster may be stuck on a finger with the help of a positioning aid for the correct placement. The positioning aid can be, for example, a w-shaped elastic part surrounding the plaster. This combination can be placed over the fingers, and when the w-shaped part is removed, the plaster sticks to the fingers. After usage, the plaster may be removed from the finger like a band-aid. In order to decrease costs, either light detectors or light sources could be placed on the air system. The plaster may alternatively form a single finger cuff.

Figure 8A:
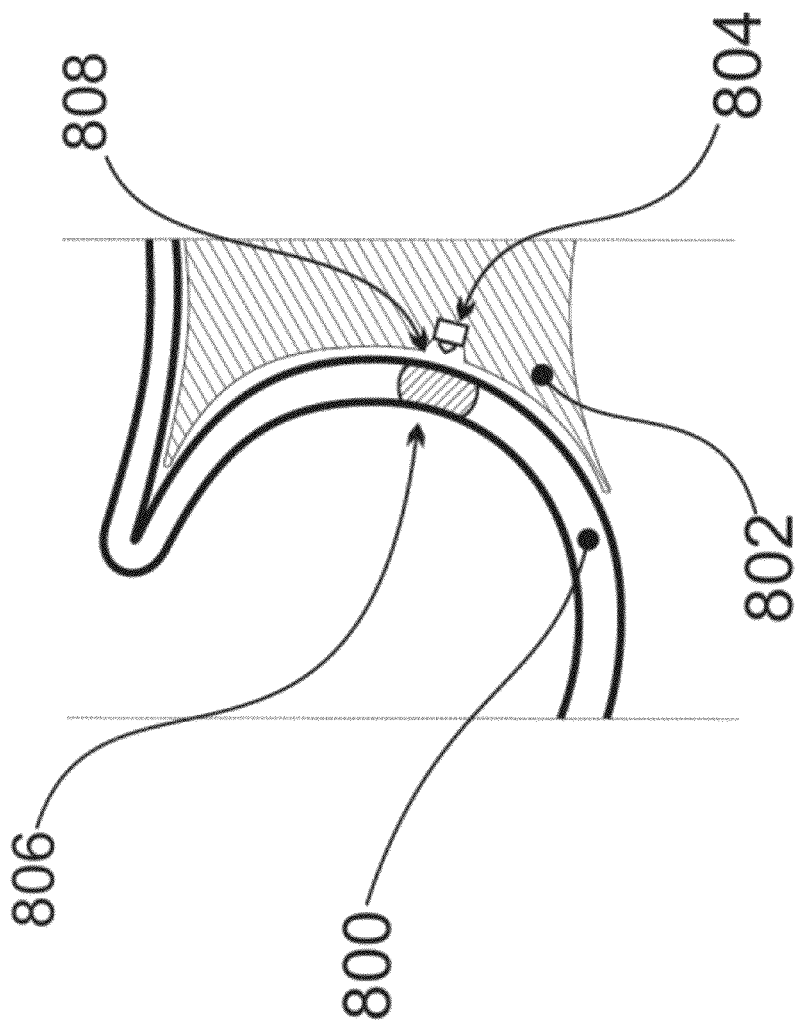
FIGS. 8a and 8b show a fluid-filled light coupling system before and after fixation of the disposable portion on the base portion.
Figure 8B:
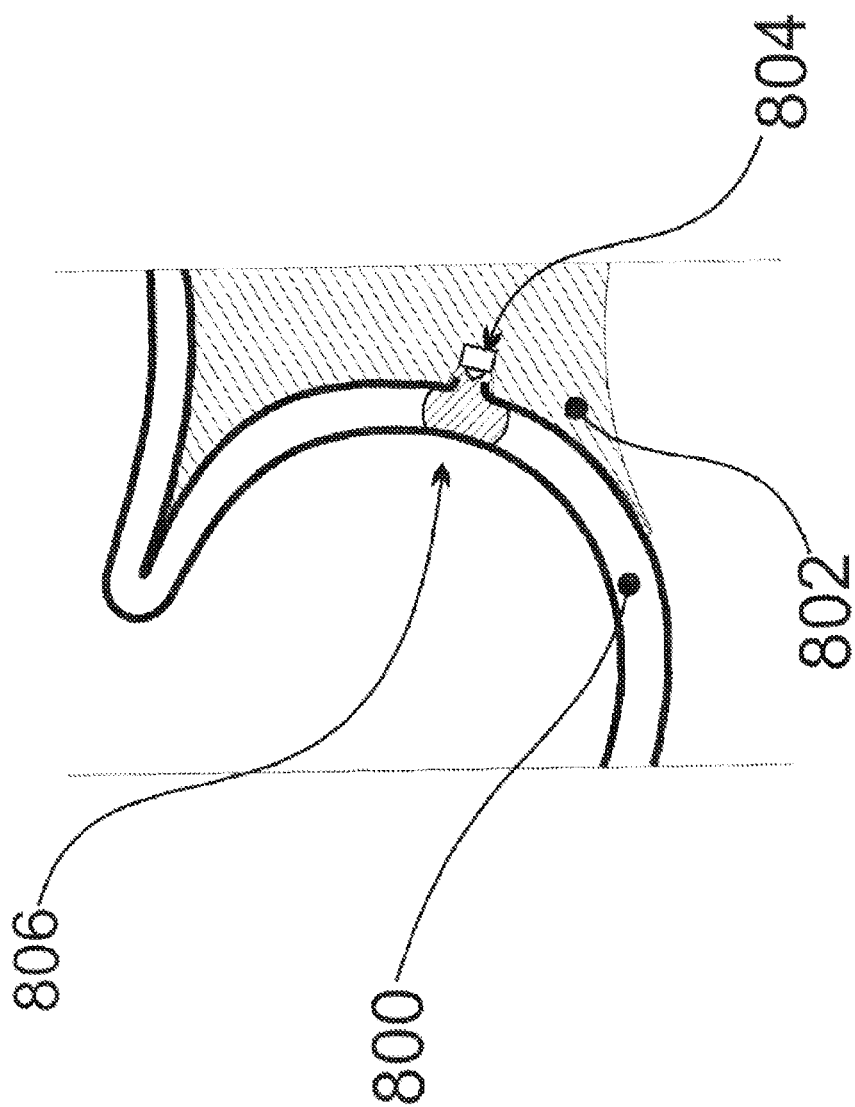

The system shown in FIGS. 8a and 8b may include a detachable and disposable portion 800 made of plastic or another formable material. The disposable portion 800 contains a reservoir 806 that is filled with a liquid. The reservoir 806 is opened when the disposable portion 800 is mounted onto a fixed portion 802. The liquid flows out of the reservoir 806 and flows into a second, empty reservoir 808, which is placed in front of a light source or detector 804. The liquid is the coupling medium between the finger and light source or detector 804. The coupling medium enhances the light propagation between finger tissue and optical sensors by avoiding the gap between the different materials.

When the disposable portion 800 is removed from the base portion 802, the liquid evaporates. The liquid may be a disinfectant that cleans the base portion 802 after the measurement is taken, for example.

In some embodiments, the sensor may include a portion that protects the sensor against unauthorized re-use. This can be achieved by electronics via encrypted authorization, or a simple fuse-like arrangement located within the cuff.

It should be understood that any of the embodiments described above can be formed as a single finger sensors as well as double finger sensors. Double finger sensors have longer measurement times due to finger switching, and also provide a safe placement for the light source and light detector, as they cannot be twisted around one finger.

While the invention has been described herein with relation to certain embodiments and applications, those with skill in the art will recognize changes, modifications, alterations, and the like which still come within the spirit of the inventive concept, and such are intended to be within the scope of the invention as expressed in the following claims.

The invention claimed is:

1. A sensor system for the measurement of one or more physiological signals comprising:
    a base portion connected to a measurement unit, the base portion being reusable; and
    a detachable portion secured to the base portion, the detachable portion being disposable;
    wherein the sensor system includes a plethysmographic (PPG) system, the PPG system including at least one light source, at least one light detector, an electrical connector to connect the at least one light source to an electrical supply, and an air system including an air supply, air connectors, and an air-cuff;
    wherein at least a part of the PPG system is located on the detachable portion;
    wherein the base portion houses at least one of the at least one light source, the at least one light detector, the electrical connector, the air supply or the air connectors; and
    wherein the detachable portion is configured to receive two neighboring fingers of a hand of a subject and the base portion is configured to be located between the two neighboring fingers when the detachable portion receives the two neighboring fingers; and
    wherein the air-cuff is located on the detachable portion.

2. A sensor system according to claim 1, wherein the at least one light detector, the electrical connector, the air supply, and the air connectors are located on the base portion.

3. A sensor system according to claim 2, wherein the at least one light source and the electrical connector are located on the detachable portion.

4. A sensor system according to claim 2, wherein the base portion includes the at least one light source and the detachable portion includes a fiber optic system.

5. A sensor system according to claim 1, wherein the at least one light source, the electrical connector, the air supplies, and the air connectors are located on the base portion.

6. A sensor system according to claim 5, wherein the at least one light detector and an electrical supply to the at least one light detector is located on the detachable portion.

7. A sensor system according to claim 5, wherein the detachable portion includes a fiber optic system.

8. A sensor system according to claim 1, wherein the detachable portion is a double finger plaster including the at least one light source, the at least one light detector, and the electrical connector.

9. A sensor system according to claim 1, wherein the detachable portion includes a liquid filled reservoir and an empty reservoir.

10. A sensor system according to claim 9, wherein the liquid is a disinfectant.

* * * * *